United States Patent
Fujikawa

(10) Patent No.: US 7,393,991 B2
(45) Date of Patent: Jul. 1, 2008

(54) PROCESS FOR PRODUCING INTERNAL OLEFIN

(75) Inventor: Nobuo Fujikawa, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 10/590,486

(22) PCT Filed: Feb. 21, 2005

(86) PCT No.: PCT/JP2005/002719

§ 371 (c)(1),
(2), (4) Date: Aug. 24, 2006

(87) PCT Pub. No.: WO2005/002818

PCT Pub. Date: Sep. 9, 2005

(65) Prior Publication Data

US 2007/0173677 A1    Jul. 26, 2007

(30) Foreign Application Priority Data

Feb. 27, 2004   (JP)   ............................. 2004-053153

(51) Int. Cl.
*C07C 5/23* (2006.01)
(52) U.S. Cl. .................................................... 585/670
(58) Field of Classification Search .................. 585/670
See application file for complete search history.

(56) References Cited

U.S. PATENT DOCUMENTS

| 4,879,429 | A | * | 11/1989 | Suzukamo et al. | .......... 585/670 |
| 5,087,793 | A | * | 2/1992 | Akiyama et al. | ............ 585/666 |
| 6,054,629 | A | * | 4/2000 | Baralt et al. | ................ 585/670 |

FOREIGN PATENT DOCUMENTS

| JP | 8 268924 | 10/1996 |
| JP | 2002 520378 | 7/2002 |
| JP | 2003 154276 | 5/2003 |
| WO | 90 03354 | 4/1990 |

* cited by examiner

*Primary Examiner*—Glenn Caldarola
*Assistant Examiner*—John C Douglas
(74) *Attorney, Agent, or Firm*—Oblon, Spivak, McClelland, Maier & Neustadt, P.C.

(57) ABSTRACT

The present invention is a method for producing an internal olefin, wherein an α-olefin containing 50 ppm water or less according to a Karl Fischer test method is contacted with a zeolite catalyst and/or a montmorillonite catalyst for the isomerization thereof and provides an industrially advantageous method for the selective internal isomerization of the raw material α-olefin using a inexpensive catalyst while preventing catalyst deterioration and side reactions such as skeletal isomerization, oligomerization and cracking.

3 Claims, No Drawings

PROCESS FOR PRODUCING INTERNAL OLEFIN

TECHNICAL FIELD

The present invention relates to a method for producing an internal olefin and, more specifically, to an efficient method for producing an internal olefin, which comprises contacting an α-olefin containing 50 ppm water or less with a zeolite catalyst and/or a montmorillonite catalyst under mild conditions for the selective internal isomerization thereof and which can prevent catalyst deterioration and side reactions such as skeletal isomerization, oligomerization and cracking.

BACKGROUND ART

Hitherto, internal olefins are used in various applications such as a base oil for petroleum drilling oils, a raw material for detergents, a raw material for paper sizing agents, a base oil or raw material for lubricant and a raw material for chemicals.

When used for the above applications, the internal olefins are required to have the following properties.

For example, for use as a base oil for petroleum drilling oils, internal olefins having 16 or 18 carbon atoms are used. These olefins are required to have adjustable pour points and kinematic viscosities, and high biodegradability.

For use as a raw material for detergents, various internal olefins having about 10 to 19 carbon atoms are used. These olefins are often required to have a particularly high linear chain content in order to improve their biodegradability.

For use as a raw material for paper sizing agents, various internal olefins having about 10 to 30 carbon atoms are used. Also, these olefins are often required to have a high linear chain content.

For use as a base oil or a raw material for lubricant, various internal olefins having about 5 to 30 atoms are mainly used. These olefins are occasionally required to have controllable pour points and kinematic viscosities, and high linear chain content.

Internal isomerization of α-olefins using metal catalysts containing Pt, Ru, Ni, etc. supported on alumina, solid acid catalysts such as zeolites (e.g. ferrierite and SAPO) or clay, or their combined metal/solid acid catalysts are known and are already industrially in practice.

Most side reactions occurring in the internal isomerization of α-olefins using combined metal/solid acid catalysts include oligomerization, skeletal isomerization and cracking.

The number of the carbon atoms of the olefin increases upon oligomerization and decreases upon cracking.

In the skeletal isomerization, the number of carbon atoms does not change. However, linear olefins are converted into branched, tri-substituted or tetra-substituted olefins depending upon the position of the double bond.

Branched olefins are also produced by oligomerization or cracking.

Although some techniques utilize the above reactions as methods for producing internal olefins, since, in recent years, the products are utilized as raw materials for detergents, drilling oils, etc., biodegradability is considered particularly important. Techniques which yield poorly biodegradable branched olefins are not favored.

It is known that skeletal isomerization and internal isomerization occur in the isomerization of an olefin using a solid acid catalyst such as zeolite, e.g. H-ZSM-5 (for example, Non-Patent Document 1).

A method is also known in which only internal isomerization is selectively allowed to occur, preventing side reactions such as skeletal isomerization, by using a catalyst such as Cr/aluminophosphate (for example, Patent Document 1), ferrierite (for example, Patent Document 2) or NiO/ZSM-5 (for example, Patent Document 3).

Techniques are further known which employ supported catalysts of Pd, etc. or catalysts whose external surface acid sites are treated with silane.

However these techniques are mainly designed to improve catalytic performance. Few improvements, in process, are made that realize mild reaction conditions which prevent catalyst deterioration and the above-mentioned side reactions.

Patent Document 1:U.S. Pat. No. 4,593,146
Patent Document 2:U.S. Pat. No. 4,727,203
Patent Document 3:U.S. Pat. No. 6,054,629
Non-Patent Document 1:J. Catal. 92(1985)

DISCLOSURE OF THE INVENTION

Under the circumstance described above, the present invention is designed to provide an efficient method for producing an internal olefin comprising contacting an α-olefin in the presence of an inexpensive zeolite catalyst and/or a montmorillonite catalyst under mild conditions, selectively internal-isomerizing, and preventing catalyst deterioration and side reactions such as skeletal isomerization, oligomerization and cracking.

The present inventors have made an earnest study for accomplishing the above object and, as a result, have found that the object can be achieved by internal isomerization of an α-olefin having a specific water content, and using inexpensive catalyst, zeolite catalyst and/or a montmorillonite catalyst.

The present invention has been completed based on the above finding.

Namely, the present invention provides:
(1) A method for producing an internal olefin, characterized in that an α-olefin containing 50 ppm water or less according to the Karl Fischer test method is contacted with a zeolite catalyst and/or a montmorillonite catalyst for the isomerization thereof;
(2) A method for producing an internal olefin as recited in (1) above, wherein the α-olefin has 8 to 24 carbon atoms.
(3) A method for producing an internal olefin as recited in (1) or (2) above, wherein a reaction temperature is 70 to 200° C.
(4) A method for producing an internal olefin as recited in any one of (1) to (3) above, wherein the α-olefin has been dehydrated by distillation or a drying agent.

BEST MODE FOR CARRYING OUT THE INVENTION

In the method for producing an internal olefin according to the present invention, an α-olefin having 8 to 24 carbon atoms, preferably 16 to 20 carbon atoms, is used as the raw material α-olefin.

The α-olefin having 8 to 24 carbon atoms may be obtained by oligomerizing α-olefin having 2 to 4 carbon atoms, preferably ethylene, using a Ziegler type catalyst.

Thus, the reaction product, i.e. low polymer of an α-olefin such as ethylene, is a mixture of 1-butene, 1-hexene, 1-octene, 1-decene, 1-dodecene, 1-tetradecene, 1-hexadecene, 1-octadecene, and 1-icocene, etc.

In the present invention, a single fraction of the above-described α-olefin low polymer or a mixed fraction having a certain range of the number of the carbon atoms may be used depending upon the use of the obtaining internal olefin.

Further, instead of the above-mentioned low polymer obtained by reacting Ziegler type catalyst with an α-olefin such as ethylene, rather an α-olefin obtained from catalytic cracking apparatuses, etc. may also be used.

In the present invention, an internal olefin is produced by internal isomerization of at least one α-olefin, selected from the above-described α-olefins having 8 to 24 carbon atoms, using a zeolite catalyst and/or a montmorillonite catalyst.

The water content of the raw material α-olefins used in the present invention is 50 ppm or less, preferably 20 ppm or less, still more preferably 10 ppm or less.

As a method for measuring the water content in an α-olefin, the Karl Fischer test method (in accordance with JIS K-2275) is used in the present invention.

The method for removing the water contained in an α-olefin is not specifically limited. The α-olefin may be passed through a drying tower charged with a drying agent. Alternatively, before the reaction, the α-olefin may be distilled for the removal of water.

As the drying tower, an ordinary fixed bed mode may be used. As the drying agent, Molecular Sieve 3A, 4A and 5A, activated alumina, or anhydrous silica gel, etc., dried at 200 to 500° C., may be used.

The drying tower may be operated at room temperature. The pressure and flow rate may be adjusted depending on the isomerization reaction conditions.

As the catalyst used in the present invention, zeolite and montmorillonite catalysts may be mentioned.

As the zeolite, natural zeolite and synthetic zeolite may be mentioned.

As the natural zeolite examples, chabazite, mordenite, erionite, faujasite and clinoptilolite are mentioned.

As the synthetic zeolite, there may be mentioned those of type A, type B, type X, type Y, type L, type omega, type MFI, etc.

Above all, MFI type zeolite is preferable. As the MFI type zeolite, ZSM-5, silicalite, etc. are suitable.

The above-mentioned zeolites may be used as the zeolite catalyst of the present invention. If necessary, they may be subjected to an acid treatment, an ammonium ion treatment, an ion exchange treatment, etc. for controlling the acidity thereof.

Particularly, a proton type zeolite having a part or whole of its cations substituted is preferred. Among them, proton-substituted H-ZSM-5 is preferred.

As the montmorillonite catalyst used in the present invention, there may be mentioned minerals of montmorillonite, nontronite, beidelite, hectorite and saponite which are classified in smectite minerals. Above all, montmorillonite is preferably used for reasons of catalytic activity, etc.

The above-mentioned clay minerals such as montmorillonite may be used as the montmorillonite catalyst of the present invention. If necessary, they may be subjected to an acid treatment, a halogenation treatment, a cation exchange treatment, etc. for controlling the acidity thereof.

As the acid treatment, there may be used, for example, a method in which the clay mineral is dispersed in an aqueous solution containing an inorganic acid such as hydrochloric acid, sulfuric acid or phosphoric acid, or an organic solvent such as alcohol. The mixture is, if necessary, heated, then filtered, dried and, if necessary, calcined.

As the halogenation treatment, there may be used, for example, a method in which the clay mineral is dispersed in an aqueous solution containing a halogen compound such as ammonium fluoride, aluminum fluoride or aluminum chloride. The mixture is, if necessary, heated, then filtered, dried and, if necessary, calcined. Alternatively, a method in which the above clay mineral is charged in a reaction tube, through which a fluorohydrocarbon is passed at a temperature of about 500° C.

As the cation exchange treatment, there may be used, for example, a method in which the above-mentioned clay mineral is dispersed in an aqueous solution containing a metal salt of various types for cation exchange treatment thereof. Thereafter, the clay mineral is filtered out and washed with water.

In the present invention, an α-olefin having 8 to 24 carbon atoms and containing 50 ppm water or less is heat treated in the presence of the thus prepared zeolite and/or montmorillonite catalysts, so that internal isomerization is allowed to occur to produce an internal olefin.

In general, in such internal isomerization, the α-olefin conversion rate is low at a low temperature, though skeletal isomerization and oligomerization hardly occur, and the majority of product is the olefin in which the double bonds are shifted to the beta- or gamma-position.

On the other hand, at a high temperature, with an increase of the conversion, the selectivity is lowered due to side reactions such as skeletal isomerization and oligomerization. Additionally, production of an olefin in which the double bond is shifted to the delta-position or the even internal-position is accelerated.

In view of the productivity and prevention of skeletal isomerization, oligomerization and cracking, therefore, the reaction temperature is usually selected from the range of 70 to 200° C., preferably 100 to 180° C.

The reaction mode is not specifically limited. Either a fixed bed flow mode or a batch (including continuously stirred tank) mode may be employed.

The reaction, which does not cause a change of a molecular weight, may be carried out generally from ambient pressure to 5 MPa, preferably from ambient pressure to 1 MPa.

Without an activation treatment by calcination, the zeolite and/or montmorillonite catalysts may be used in the invention after pre-treatment with nitrogen or air at a temperature of about 100 to 500° C.

When a fixed bed flow system is employed as the reaction mode, LHSV (liquid hourly space velocity) selected is in a range of 0.1 to 10 $h^{-1}$, preferably 0.5 to 4 $h^{-1}$, considering the conversion of α-olefin and productivity.

When the reaction mode is a batch system, the amount of the zeolite and/or montmorillonite catalysts used is in the range of generally from 1 to 60 parts by mass, preferably 10 to 50 parts by mass, more preferably from 20 to 40 parts by mass, with respect to 100 parts by mass of the raw material α-olefin.

In this case, the reaction time is affected by the reaction temperature and desired α-olefin conversion, etc. and thus may not be determined indiscriminately. Generally, however, a reaction time of from about 30 minutes to 20 hours is sufficient. Preferably the reaction time is about 1 to 10 hours.

Thus, by using a zeolite catalyst and/or a montmorillonite catalyst and by specifying the water content of an α-olefin, it is possible to selectively internal-isomerizes the α-olefin under relatively mild conditions.

Also, the desired internal olefin may be obtained with a good yield, because catalyst deterioration and undesirable side reactions such as skeletal isomerization, oligomerization and cracking can be prevented.

Further, since commercial product may be obtained from the reaction product without distillation, a distillation tower, etc. for the removal of oligomers, etc. are unnecessary and, hence, the method is highly economical.

In addition, when the used catalysts are to be regenerated, a catalyst regeneration system capable of conducting operations such as washing, drying and, calcination may be employed depending upon the reaction mode. However, the zeolite and/or montmorillonite catalysts used in the present invention are generally inexpensive, and it is possible to design a sufficiently economical process even if exchange of the catalyst is a prerequisite.

Described below are applications of the internal olefin obtained by the method of the present invention and the advantages of the method of the present invention:

(1) Base Oil for Petroleum Drilling Oils

For this use, internal olefins having 16 or 18 carbon atoms are used. The olefins are required to have adjustable pour points and kinematic viscosities and to have high biodegradability. In the present invention, such requirements may be met by using an α-olefin having a high linear chain content as a raw material, and by controlling the double bond distribution.

(2) Raw Material for Detergents

For this use, internal olefins having about 10 to 19 carbon atoms are used. The olefins are often required to have a particularly high linear chain content.

In the present invention in which skeletal isomerization can be effectively prevented, such a requirement may be met by using an α-olefin having a high linear chain content as a raw material.

(3) Raw Material for Paper Sizing Agents

For this use, various internal olefins having 10 to 30 carbon atoms are used. The olefins are often required to have a high linear chain content. Similar to (2) above, such a requirement may be met by using an α-olefin having a high linear chain content as a raw material.

(4) Base Oil or Raw Material for Lubricant

For this use, various internal olefins mainly having 6 to 30 carbon atoms are used.

The olefins are occasionally required to have adjustable pour points and kinematic viscosities and high biodegradability. In the present invention, such requirements may be met by using an α-olefin having a high linear chain content as a raw material and by controlling the double bond distribution.

EXAMPLE

The present invention will be described in further detail below by way of Examples and Comparative Examples. However, the present invention is not restricted to these Examples in any way.

Example 1

In a one inch diameter stainless steel pipe (length: 0.6 m, inside diameter: 25 mm), 200 ml of Molecular Sieve 3A were charged. A nitrogen gas was passed through the pipe at a rate of 100 ml/min and drying was carried out at 300° C. for 24 hours to obtain a drying tower.

In a 12 mm diameter stainless steel reaction tower (length: 1.1 m, inside diameter: 10 mm), 50 ml of HMFI-90 (manufactured by SUD-CHEMIE INC., proton type MFI zeolite catalyst) were charged. A nitrogen gas was passed through the reaction tower at a rate of 100 ml/min and pretreatment was carried out at 300° C. for 4 hours.

The top of the drying tower was connected to a lower part of the reaction tower. Then, from a lower part of the drying tower, 1-hexadecene [LINEALENE 16 manufactured by Idemitsu Petrochemical Co., Ltd. (linear α-olefins: 92% by mass, branched α-olefins: 8% by mass, linear chain content: 92%)] containing 60 ppm water as measured by Karl Fischer method at 20° C. was fed at a rate of 100 ml/hour in an upward flow.

The water content at the outlet of the drying tower (at an inlet of the reaction tower) was 5 ppm.

When 1-hexadecene liquid flew out from the reaction tower outlet, the temperature of the reaction tower was raised to 140° C. to start the reaction.

The initial reaction activity became stable after 72 hours. The analysis of the reaction liquid obtained after 200 hours revealed that the conversion of 1-hexadecene was 96.0%, the oligomer yield was 1.0% by mass and the linear chain content remained unchanged (92.0%).

The results are summarized in Table 1.

Comparative Example 1

A reaction was carried out under the same conditions as those in Example 1 except that 1-hexadecene containing 60 ppm water was not passed through the drying tower.

The initial reaction activity became stable after 72 hours. The analysis of the reaction liquid obtained after 200 hours revealed that the conversion of 1-hexadecene was 70.0%, the oligomer yield was 0.4% by mass and the linear chain content remained unchanged (92.0%).

The results are summarized in Table 1.

Comparative Example 2

In Comparative Example 1, the reaction temperature was raised from 145° C. to 180° C. in order to increase the conversion of 1-hexadecene.

The analysis of the reaction liquid obtained 200 hours after the temperature had increased to 180° C. revealed that the conversion of 1-hexadecene was 96.0%, the oligomer yield was 3.2% by mass and the linear chain content reduced to 86.0%.

The results are summarized in Table 1.

TABLE 1

|  | Example 1 | Comparative Example 1 | Comparative Example 2 |
| --- | --- | --- | --- |
| Conversion (%) | 96.0 | 70.0 | 96.0 |
| Linear chain content (%) | 92.0 | 92.0 | 86.0 |
| Linear α-olefins (% by mass) | 3.7 | 27.6 | 3.4 |
| Branched α-olefins (% by mass) | 0.3 | 2.4 | 0.6 |
| Linear internal olefins (% by mass) | 87.4 | 64.0 | 79.8 |
| Branched internal olefins (% by mass) | 7.6 | 5.6 | 13.0 |
| Oligomer (% by mass) | 1.0 | 0.4 | 3.2 |
| Yield of linear internal olefins (%) | 87.4 | 64.0 | 79.8 |

INDUSTRIAL APPLICABILITY

According to the present invention, internal olefins are produced efficiently with an industrial advantages because catalyst deterioration and side reactions, such as skeletal isomerization, oligomerization and cracking, are prevented by subjecting an α-olefin containing 50 ppm water or less to selective internal isomerization under mild conditions in the presence of a zeolite catalyst and/or a montmorillonite catalyst.

The invention claimed is:

1. A method for producing a linear internal olefin, comprising:
   contacting an α-olefin with a zeolite catalyst and/or a montmorillonite catalyst to isomerize the α-olefin and obtain the linear internal olefin;
   wherein:
   the α-olefin contains 50 ppm water or less according to the Karl Fischer test method; and
   contacting the α-olefin with the zeolite catalyst and or the montmorillonite is catalyst comprises contacting at a reaction temperature of from 140 to 180° C.

2. The method for producing an internal olefin as recited in claim 1, wherein the α-olefin has 8 to 24 carbon atoms.

3. The method for producing an internal olefin as recited in claim 1 or claim 2, wherein the α-olefin is dehydrated by distillation or a drying unit.

* * * * *

UNITED STATES PATENT AND TRADEMARK OFFICE
CERTIFICATE OF CORRECTION

PATENT NO.         : 7,393,991 B2
APPLICATION NO. : 10/590486
DATED              : July 1, 2008
INVENTOR(S)        : Fujikawa It is certified that error appears in the above-identified patent and that said Letters Patent is hereby corrected as shown below:

On the title page, Item (87), the PCT publication number is incorrect. Item (87) should read:

-- (87)  PCT Pub. No.: WO2005/082818
         PCT Pub. Date: Sep. 9, 2005 --

Signed and Sealed this

Nineteenth Day of August, 2008

JON W. DUDAS
*Director of the United States Patent and Trademark Office*